United States Patent [19]

Rideout et al.

[11] 4,299,824

[45] Nov. 10, 1981

[54] SUBSTITUTED PYRAZOLO PYRIMIDINE RIBOSIDE COMPOUNDS, PHARMACEUTICAL COMPOSITIONS AND METHOD OF USE

[75] Inventors: Janet L. Rideout, Raleigh; Thomas A. Krenitsky; Gertrude B. Elion, both of Chapel Hill, all of N.C.

[73] Assignee: Burroughs Wellcome Co., Research Triangle Park, N.C.

[21] Appl. No.: 159,245

[22] Filed: Jun. 13, 1980

[30] Foreign Application Priority Data

Jun. 14, 1979 [GB] United Kingdom ............... 20700/79

[51] Int. Cl.$^3$ ....................... A61K 31/70; C07H 19/18
[52] U.S. Cl. ..................................... 424/180; 536/24; 536/26; 536/28; 544/262
[58] Field of Search ............................ 536/24, 26, 28; 424/180; 544/262

[56] References Cited

U.S. PATENT DOCUMENTS

| | | | |
|---|---|---|---|
| 3,074,929 | 1/1963 | Hitchings et al. | 536/26 |
| 3,074,930 | 1/1963 | Hitchings et al. | 536/26 |
| 3,269,917 | 8/1966 | Imada et al. | 536/24 |

FOREIGN PATENT DOCUMENTS 760283 12/1970 Belgium ............................. 544/262

Primary Examiner—Johnnie R. Brown
Attorney, Agent, or Firm—Donald Brown

[57] ABSTRACT

4-Alkenylthio-1-$\beta$-D-ribofuranosylpyrazolo[3,4-d]-pyrimidines are active against coccidia in vivo, and unlike the 4-methylthio analogue, are non-toxic. Methods for the preparation and use of the compounds, intermediates in the preparation and formulations of the compounds are also described.

12 Claims, No Drawings

SUBSTITUTED PYRAZOLO PYRIMIDINE RIBOSIDE COMPOUNDS, PHARMACEUTICAL COMPOSITIONS AND METHOD OF USE

The present invention relates to 4-alkenylthio-1-β-D-ribofuranosylpyrazolo[3,4-d]pyrimidine derivatives which are useful as antiprotozoal agents, especially for treating or preventing coccidiosis.

Coccidiosis is caused by protozoa of the genus Eimeria, which infect susceptible hosts by contact with faeces of diseased animals. It is therefore particularly damaging when animals are kept in close contact, and is thus the most important disease of poultry. Various therapeutic and prophylactic agents are known for combatting coccidiosis and are used with differing degrees of success. These are usually administered throughout the life of animals and there is consequently a risk of the protozoa developing resistance to one or more of these agents.

4-Methylthio-1-β-D-ribofuranosylpyrazolo[3,4-d]pyrimidine and close analogues were prepared as potential anticancer agents, [J-L. G. Montero et al., *J. Hetero Chem.*, 14, 483, (1977); R. P. Panzica et. al., R. E. Harman, R. K. Robins and L. B. Townsend, (Eds), *Chemistry and Biology of Nucleosides and Nucleotides*, Academic Press, New York (1978), 121–134] but no other type of biological activity has been disclosed.

The 4-methylthio-pyrazolo[3,4-d]pyrimidine riboside has now been tested against coccidia and whilst it has good in vitro activity, it was found to be highly toxic, causing unacceptable fatalities in chickens.

It has now been found that 4-alkenylthio-pyrazolo[3,4-d]pyrimidine ribosides are also active against protozoa of the genus Eimeria. In contrast with the known 4-methylthio derivative, these compounds have surprisingly low toxicity towards the host animal and are therefore suitable for treating or preventing coccidiosis in poultry.

According to the present invention therefore there is provided a compound of formula (I)

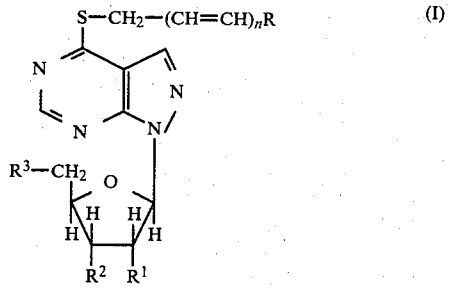

wherein n has the value 1 or 2 and R is a phenyl group, optionally substituted with one or more lower alkyl, lower alkoxyl, trifluoromethyl, benzyloxy, phenoxy, amino, mono- or di- lower alkylamine or hydroxyl groups or halogen atoms and either $R^1$, $R^2$ and $R^3$ are the same and are hydroxy or acyloxy groups, —O—CO—$R^4$ wherein $R^4$ is a hydrogen atom or a lower alkyl or substituted or unsubstituted phenyl group or else $R^1$ and $R^2$ are hydroxyl or acyloxy groups and $R^3$ is a phosphate group or a salt thereof.

It is preferred that n has the value 1.

When $R^4$ is present as a phenyl group, it may be optionally substituted with one or more of the substituents commonly known in the art and used as substituents for benzoyl esters of nucleosides and nucleotides such as amino, hydroxy, nitro, lower alkyl and lower alkoxy groups and halogen atoms.

As used herein the terms "lower alkyl group" and "lower alkoxyl group" refer to such groups having from 1 to 4 carbon atoms.

If $R^3$ represents a salt of phosphate group, it is preferred that it is a pharmaceutically acceptable salt, such as the sodium or potassium salt in a mono- or dibasic form.

The most preferred compounds of formula (I) are 4-cinnamylthio-1-β-D-ribofuranosylpyrazolo[3,4-d]pyrimidine, its phosphate ester and salts thereof.

Compounds of formula (I) may be prepared either by modification of the 4-substituent of a 1-β-D-ribofuranosylpyrazolo[3,4-d]pyrimidine (the precursor), or by linking the ribose moiety to a pyrazolo[3,4-d]pyrimidine derivative already bearing the required group at the 4-position.

According to a second aspect of the present invention there is therefore provided a process for producing compounds of formula (I) comprising either (a) the reaction between the precursor, a 4-(substituted)-1-β-D-ribofuranosylpyrazolo[3,4-d]pyrimidine derivative and a compound R(CH=CH)$_n$CH$_2$X wherein n and R are as hereinbefore defined and either (i) X is a halogen atom and the 4-substituent of the precursor is a thio group and the reaction is performed in the presence of an organic or inorganic base or basic resin in an aqueous, a lower alcoholic or an aprotic solvent; or (ii) X is an appropriate mercaptide radical and the 4-substituent of the precursor is a halogen atom or an alkylthio or aralkylthio group and the reaction is performed in the presence of an aprotic solvent; or (b) the reaction of a compound of formula (II)

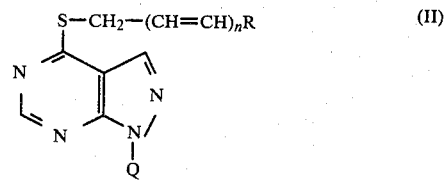

wherein n and R are as hereinbefore defined and Q is an appropriate leaving atom or group, with a riboside donor system by chemical, enzymatic or microbiological methods known in the art of nucleoside synthesis, and optionally thereafter forming appropriate organic or phosphate esters, and salts of the latter, by techniques known in the art.

As used herein in relation to the precursor of method (a); the term "4-(substituted)-1-β-D-ribofuranosylpyrazolo[3,4-d]pyrimidine derivative" includes such organic and phosphate esters, and salts of the latter, as are appropriate to the final product of the process.

In a method (a) (i) the halogen atom may be a chlorine, bromine or iodine atom. The base used in this method may be an alkali or alkaline earth metal hydroxide or alkoxide, quaternary ammonium hydroxide, hydrogen carbonate or carbonate, or a basic resin such as Dowex 1-X8 (bicarbonate) [Dowex is a Registered Trade Mark] supplied by Bio-Rad Laboratories, California, U.S.A. The solvent may be water, a lower alcohol, such as methanol or ethanol or an aprotic solvent such as N,N-dimethylformamide, dimethylsulphoxide or hexamethylphosphoric triamide although N,N-dimethylformamide is preferred.

When method (a) (ii) is employed, it is desirable to protect the hydroxyl groups of the ribosyl moiety of the precursor with blocking groups, that is with acyl groups provided by the use of such acylating agents as acid anhydrides, e.g. acetic anhydride, or acid chlorides, e.g. benzoyl chloride. These blocking groups may subsequently be removed by conventional methods of deacylation such as treatment with alcoholic ammonia or an alkali metal alkoxide followed by neutralisation of the base.

Method (a) (ii) may be applied to any suitable 4-halogeno-, 4-alkylthio-, or 4-aralkylthio- substituted precursor and can thus be used to interconvert compounds of formula (I) by nucleophilic displacement of the 4-substituent. The radical X may conveniently be a sodium or potassium mercaptide, however other metal mercaptides are also suitable. In this particular method it is preferred that the 4-substituent of the precursor is a halogen atom or a lower alkylthio group, especially a methylthio group.

Chemical processes may be employed in method (b), using a compound of formula (II) in which Q is a hydrogen or a metal atom, e.g. an alkali metal atom such as sodium, or other leaving group, and the riboside donor system comprises a reactive ribose derivative such as a 1-chlororibose derivative, the reaction being performed in an appropriate solvent system such as an aprotic solvent, e.g. dimethylformamide or acetonitrile. However, it is preferred that enzymatic or microbiological processes are used.

Such enzymatic processes include the preparation of compounds of formula (I) from the appropriate free base using phosphorylase-type enzymes in a manner known in the art; see for instance T. A. Krenitsky, G. B. Elion, R. A. Strelitz, G. H. Hitchings, *J. Biol. Chem.*, 242, 2675–2682, (1967); U.K. Patent Application No. 45668/77 see also European Patent Application No. 78 101 295.0 in which case, Q is hydrogen and the riboside donor system consists of appropriate purine and/or pyrimidine-1-β-D-ribosides and/or ribose-1-phosphate and the appropriate enzyme or enzymes.

Alternatively the ribosidation may be accomplished by microbiological processes such as that disclosed in German Offenlegungsschrift No. 2 209 078 wherein Q is hydrogen and the riboside donor system comprises bacteria of the genera Brevibacterium, Arthrobacter, Corynebacterium or Micrococcus and the culture medium which includes glucose.

Whenever the compound of formula (I) is required to carry acyloxy groups for $R^1$, $R^2$ and $R^3$, a corresponding starting compound having hydroxy groups in these positions is reacted with acylating agents such as acetic anhydride or benzoyl chloride according to conventional methods. Acylation may be effected before or after other synthetic steps except that when enzymatic or microbiological processes are to be used for the ribosidation of a compound of formula (II) the acylation must be performed after the ribosidation.

When $R^3$ of the desired compound of formula (I) is to be a phosphate group, this may be introduced into the corresponding compound having a hydroxyl group in that position by phosphorylation using traditional phosphorylating agents such as trialkyl phosphate, e.g. triethyl phosphate, with a phosphorus oxyhalide such as phosphoryl chloride. When this technique is used it is advantageous to block the 2' and 3' positions of the ribose moiety either by blocking only these two positions by using appropriate conditions or by blocking the 2', 3' and 5' positions and then selectively deblocking the 5' position. The latter course may be facilitated by first blocking the 5' position with a bulky group, such as a trityl group or a t-butyldimethylsilyl group, then blocking the 2' and 3' positions by conventional means, and finally deblocking the 5' position. After phosphorylation the 2' and 3' positions are then deblocked to afford the required compound.

Rather than block the 2' and 3' positions as described above, it is preferred to use phosphoryl chloride in the presence of a trialkylphosphate (preferably triethyl phosphate) and a trace of water at a temperature of about 0° C. or below. This forms the 5'-phosphate dichloridate which is then hydrolysed to the 5'-phosphate upon treatment with water at slightly basic pH.

Salts of phosphate-substituted compounds of formula (I) are obtained by conventional reactions between the phosphate derivative and an appropriate base in aqueous media.

The precursors for use in method (a) may be well known compounds such a 4-hydroxy-, 4-thio, or 4-methylthio-1-β-D-ribofuranosylpyrazolo[3,4-d]pyrimidine derivatives, or may be obtained therefrom by conventional techniques. These ribosides may have been prepared from the corresponding free pyrazolo[3,4-d]pyrimidine bases by ribosidation as described for method (b) above.

The 4-halogeno precursor can be derived by treating an acylated derivative of 4-hydroxy-pyrazolo[3,4-d]pyrimidine riboside with a phosphoryl halide, the corresponding Villsmeier regent or other known halogenating reagents. Alternatively, treatment of the 4-thio analogue with chlorine or bromine and the appropriate hydrogen halide in a lower alcohol at low temperature, affords the 4-halogeno precursor.

The 4-thio substituted precursor may be obtained from the acylated 4-halogeno-pyrazolo[3,4-d]pyrimidine riboside by treatment of the latter with thiourea, phosphorus pentasulphide or sodium hydrosulphide The 4-alkylthio, and 4-aralkylthio substituted precursors may be derived from other compounds of this class, from the 4-halogeno precursor or from the 4-thio precursor by process (a), mutatis mutandis. Compounds of formula (II) for use in method (b), i.e. the 1-unsubstituted analogues of compounds (I), may be produced by the techniques described above for the production of precursors and by method (a) above, mutatis mutandis.

In a third aspect of the present invention there is provided a 1-β-D-ribofuranosylpyrazolo[3,4-d]pyrimidine derivative of general formula (III)

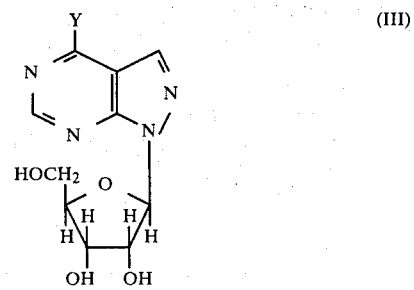

wherein Y is a halogen atom.

In a fourth aspect of the present invention there is provided a compound of general formula (IV)

$$S-CH_2-(CH=CH)_nR \quad (IV)$$

(structure: pyrazolo[3,4-d]pyrimidine ring with S—CH$_2$—(CH=CH)$_n$R substituent at position 4 and Q at N)

wherein n, R and Q are as hereinbefore defined.

Compounds of formula (I) as hereinbefore defined are useful for treating coccidial infections, or preventing them, in livestock. The compounds may be administered alone, or in association with carriers.

In a further aspect of the present invention there is provided a pharmaceutical formulation comprising at least a compound of formula (I) for administration to livestock.

It may be convenient to administer the compounds in association with various carriers and additives to facilitate that administration. In particular, the compounds may be administered in the foodstuff or drinking water provided for the livestock.

The present invention, in a further aspect, therefore provides a pharmaceutical composition comprising a compound of formula (I) in association with a carrier therefor.

Carriers are materials which are useful for the purpose of administering the compound while being otherwise inert as regards interaction with the compound and non-toxic to the recipient of the composition. It is particularly preferred that the carrier is the foodstuff or drinking water provided for the livestock.

When incorporated into foodstuff or drinking water the compounds may be administered at a concentration of about 10 ppm to 400 ppm, preferably 50 ppm to 200 ppm and most preferably 100 ppm.

4-Cinnamylthio-1-β-D-ribofuranosylpyrazolo[3,4-d]pyrimidines has not been observed to cause any toxicity or reduction in weight gain in chicks when administered at a concentration of 800 ppm of the diet.

Some compounds of formula (I) are insufficiently soluble for administration in drinking water. In this case the phosphate ester, or more preferably, a salt thereof can be employed.

In a further aspect of the present invention there is provided a method for preventing or treating coccidial infections of livestock comprising the administration of an effective anticoccidial amount of a compound of formula (I) or a formulation or composition thereof.

The invention will now be illustrated by the following Examples, which should not be construed as limiting the invention in any way.

EXAMPLE 1

Preparation of 4-cinnamylthio-1-β-D-ribofuranosylpyrazolo[3,4-d]pyrimidine.

Cinnamyl bromide (3.04 g) was added to a stirred solution of 4-mercapto-1-β-D-ribofuranosylpyrazolo[3,4-d]-pyrimidine (4.0 g) and potassium carbonate (2.13 g) in N,N-dimethylformamide. The solution was heated (40° C. on an oil bath) for 2 hours. After cooling the reaction mixture was poured into water (0.6 l) and the resultant precipitate was collected and washed with water. The 4-cinnamylthio-1-β-D-ribofuranosylpyrazolo[3,4-d]pyrimidine so obtained was recrystallised from methanol, washed with water and dried (in vacuo at 55° C.), yield 3.2 g, m.p. 165°-166° C.

EXAMPLE 2

Preparation of 4-mercapto-1-(2,3,5-tri-O-acetyl-β-D-ribofuranosyl)-pyrazolo[3,4]pyrimidine 4-Mercapto-1-β-D-ribofuranosylpyrazolo[3,4-d]pyrimidine (1.0 g) and potassium carbonate (0.48 g) were added to acetic anhydride (5 ml). The reaction was stirred at ambient temperature for 19 hours and heated at 70° C. for 1.5 hour. Methanol was added and the whole was taken to dryness in vacuo. Water was added to the residue and it was filtered in vacuo. The aqueous filtrate was extracted 3 times with chloroform. The combined chloroform extracts were dried over magnesium sulfate, filtered and taken to dryness in vacuo. The solid, 4-mercapto-1-(2,3,5-tri-O-acetyl-β-D-ribofuranosyl)pyrazolo[3,4-d]pyrimidine (1.0 g, 70%), was collected and dried in vacuo at 70° C.

| Analysis Calc'd for C$_{16}$H$_{18}$N$_4$O$_7$S . ½H$_2$O | | | |
|---|---|---|---|
| Theory: C: 45.82% | H: 4.57% | N: 13.36% | S: 7.64% |
| Found: C: 45.85% | H: 4.20% | N: 13.20% | S: 7.63% |

EXAMPLE 3

Preparation of 4-Cinnamylthio-1-(2,3,5-tri-O-acetyl-β-D-ribofuranosyl)pyrazolo[3,4-d]pyrimidine A suspension of 4-mercapto-1-(2,3,5-tri-O-acetyl-β-D-ribofuranosyl)pyrazolo[3,4-d]pyrimidine (1.0 g) and potassium carbonate (0.37 g) in N,N-dimethylformamide was stirred for 10 minutes and then cinnamyl bromide (0.53 g) was added. After stirring for 3 hr. at 40° C. the solution was filtered and 100 ml chloroform was added. The solution was extracted with water. The chloroform layer was dried, filtered and taken to dryness on a rotary evaporator. The residue was purified on a column of silica gel using chloroform as the eluant. The fractions containing the product were pooled and taken to dryness in vacuo. The residue was dissolved in chloroform, filtered through a Millipore filter in vacuo and evaporated in vacuo, to give the product 4-cinnamylthio-1-(2,3,5-tri-O-acetyl-β-D-ribofuranosyl)-pyrazolo[3,4-d]pyrimidine as a glass.

| Analysis Calc'd for C$_{25}$H$_{26}$N$_4$O$_7$S | | | |
|---|---|---|---|
| Theory C: 57.02% | H: 4.98% | N: 10.64% | S: 6.09% |
| Found C: 57.28% | H: 4.92% | N: 10.22% | S: 5.85% |

EXAMPLE 4

Preparation of 4-Cinnamylthio-1-β-D-ribofuranosylpyrazolo[3,4-d]pyrimidine 5'-monophosphate disodium salt The 4-cinnamylthio-1-β-D-ribofuranosylpyrazolo[3,4-d]pyrimidine of Example 1 (0.5 g) was added to triethyl phosphate (4 ml). The mixture was stirred and cooled in a stoppered flask (on −10° C. bath). Phosphorus oxychloride (0.48 ml) was added all at once. The reaction was stirred at −10° C. for 10 minutes and then at 0° for 45 minutes. The reaction was then maintained at 0° to +5° C. for 25 minutes more. The solution was poured onto ice and 2 N sodium hydroxide was added to give pH 7. The solution was extracted with chloroform and then ether. The aqueous phase was adjusted to give pH 7.58.

Ether was removed in vacuo from the neutralized solution (at 30° for 15 min.). One half of this solution was applied to a column containing Amberlite XAD-resin (200 ml) which had been equilibrated with water. The column was washed with three column volumes of water to elute sodium phosphate. The nucleotide was eluted with eight column volumes of ethanol in water (1:1).

The remaining half of the neutralized solution was treated similarly using a 100 ml column of resin.

Both nucleotide pools were combined and lyophillized. The lyophillized powder was dissolved in water (15 ml) and applied to a 5×100 cm column containing Bio Gel P-2. The nucleotide was eluted with water. Fractions containing the nucleotide were pooled and lyophillized. The powder was dissolved in water (5 ml) and precipitated by adding n-propanol (50 ml). This step was repeated and the final precipitate was lyophillized. The overal yield of 4-cinnamythio-1-β-D-ribofuranosylpyrazolo[3,4-d]pyrimidine 5'-monophosphate disodium salt, was 60% (0.36 g). Purity was estimated by high performance liquid chromatography to be 99%.

EXAMPLE 5

By a method exactly analogous to that of Example 1, the following were prepared.

| Example | Halide | Duratio (hours) | Product (1-B-D-ribofuranosyl-pyrazolo(3,4-d)-pyrimidine | m.pt (°C.) |
|---|---|---|---|---|
| 5(a) | Cl | 20 (at ambient temperature) | 4-(5-phenyl-2,4-pentadienyl-thio) | 145–149 |
| 5(b) | Cl | 20 | 4-(4-chlorocinna-mythio) | 113–116 |
| 5(c) | Cl | 20 | 4-(3,4-dichlorocinna-mythio) | 62–67 |
| 5(d) | Cl | 4 | 4-(2,4-dichlorocinna-mylthio) | 96(soften 90) |
| 5(e) | Cl | 0.5 | 4-(3-trifluoromethyl-cinnamylthio) | 105–100 |

EXAMPLE 6

In order to assess the activity of compounds of formula (I) against coccidia, the compounds were administered to groups of 5 male Ross Ranger chicks (7 days old), at various dosages in the diet, for 6 days. The chicks were each infected with *Eimeria tenella* and *E. acervulina* one day after the begining of the medication. The compounds cleared chicks of *E. tenella* only, as indicated in Table I below. No obvious signs of toxicity were observed during this experiment.

TABLE I

Number of chicks cleared of *E. tenella* by administration of compounds of formula (I) at various dose levels

| Compound Example No. | Dose levels (ppm of diet) | | | |
|---|---|---|---|---|
| | 200 | 100 | 50 | 25 |
| 1 | 5 | 5 | 5 | 5 |
| 3 | 5 | NT | 5 | 1 |
| 4 | 5 | 5 | 5[5] | 5[4] |

TABLE I-continued

Number of chicks cleared of *E. tenella* by administration of compounds of formula (I) at various dose levels

| Compound Example No. | Dose levels (ppm of diet) | | | |
|---|---|---|---|---|
| | 200 | 100 | 50 | 25 |
| 5(a) | 5 | NT | 5 | 1 |
| 5(b) | 5 | 5 | 0 | 0 |
| 5(c) | 2 | NT | NT | NT |
| 5(d) | 2 | NT | NT | NT |
| 5(e) | NT | NT | NT | NT |

[ ], indicates result of repeat experiment
NT, not tested.

EXAMPLE 7

Tolerance of Chicks to 4-cinnamylthio-1-β-D-ribofuranosylpyrazolo[3,4-d]pyrimidine The compound of Example 1 was administered at various dosages to groups of 15 uninfected 7-day old male Ross Ranger chicks for 8 days. At the end of that period the weight gain of each group of chicks was recorded as a percentage of the weight gain of an untreated control group (Table II).

TABLE II

| Group | Treatment (ppm of diet) | Weight gain (%) |
|---|---|---|
| 1 | 100 | 102.2 |
| 2 | 50 | 110.5 |
| 3 | 25 | 108.4 |
| 4 | 12.5 | 107.4 |
| 5 | untreated | 100 |

EXAMPLE 8

The compound of Example 1 was tested in vitro for activity against coccidia of the species *Eimeria tenella*. Cell cultures were infected with sporozoite suspension of *E. tenella* immediately after addition of the compounds. Serial dilutions of formulations containing the compounds were made in the range of 19 μg/l to 20 mg/l in order to determine the minimum active concentration. After incubation for 96 hours the cultures were fixed and the cells were stained with 0.1% toluidine blue. The stained cultures were examined microscopically for presence of parasites. The compound cleared the cell cultures of *E. tenella* at all concentrations down to 78 μg/l.

We claim:

1. A compound of formula (I)

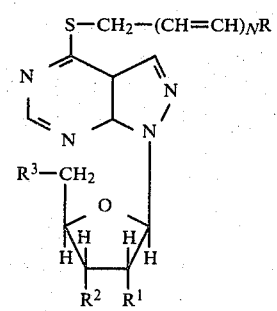

wherein n has the value 1 or 2 and R is phenyl, phenyl bearing one or more substitutents selected from the group consisting of phenyl, lower alkyl, lower alkoxyl, trifluoromethyl, benzyloxy, phenoxy, amino, mono- or di- lower alkyl amino, hydroxyl and halogen and either R¹, R² and R³ are the same and are hydroxy or acyloxy groups, —O—CO—R⁴ wherein R⁴ is hydrogen, lower alkyl, phenyl or phenyl substituted by amino, hydroxy, nitro, lower alkyl, lower alkoxy or halogen or R¹ and R² may be hydroxyl or acyloxy groups as hereinbefore defined and R³ is a phosphate group or a pharmaceutically acceptable salt thereof.

2. A compound according to claim 1 wherein n has the value 1.

3. A compound according to claim 1 wherein R is an unsubstituted phenyl group.

4. A compound according to claim 1 wherein R¹ and R² are hydroxyl and R³ is a hydroxyl or phosphate group or a salt thereof.

5. A compound of formula (IV)

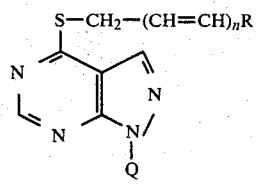 (IV)

wherein n has a value of 1 or 2, R is phenyl, phenyl having one or more substituents selected from the group consisting of lower alkyl, lower alkoxy, amino, hydroxyl and halogen and Q is hydrogen or an alkali metal atom.

6. 4-cinnamylthio-1-β-D-ribofuranosyl)pyrazolo[3,4-d]pyrimidine.

7. The salt of claim 1 in which the salt is 4-cinnamylthio-1-β-D-ribofuranosyl)pyrazolo[3,4-d]pyrimidine 5'monophosphate disodium.

8. A pharmaceutically acceptable salt of the compound of claim 6.

9. A pharmaceutically acceptable sodium or potassium salt of the compound of claim 1.

10. A pharmaceutical composition for use in combatting coccidiosis comprising an effective coccidiosis combatting amount of a compound or salt of claims 1, 7, 8, or 9 in association with a carrier therefor.

11. A method for combatting coccidial infections of livestock comprising the administration of an effective, non-toxic coccidiosis combatting amount of the compound or salt of claim 1, 7, 8 or 9.

12. A method according to claim 11 wherein the compound or salt is administered in foodstuff or drinking water in a concentration of from about 25 ppm to 400 ppm.

* * * * *